(12) United States Patent
Bilgic

(10) Patent No.: US 9,259,376 B2
(45) Date of Patent: Feb. 16, 2016

(54) PROCESS FOR DRY POWDER FORMULATIONS

(75) Inventor: Mahmut Bilgic, Istanbul (TR)

(73) Assignee: Sima Patent ve Lisanslama Hizmetleri Ltd. Sti., Esenler/Istanbul (TR)

( * ) Notice: Subject to any disclaimer, the term of this patent is extended or adjusted under 35 U.S.C. 154(b) by 151 days.

(21) Appl. No.: 13/701,599

(22) PCT Filed: Jun. 2, 2011

(86) PCT No.: PCT/TR2011/000142
§ 371 (c)(1),
(2), (4) Date: Apr. 22, 2013

(87) PCT Pub. No.: WO2011/152804
PCT Pub. Date: Dec. 8, 2011

(65) Prior Publication Data
US 2013/0202778 A1    Aug. 8, 2013

(30) Foreign Application Priority Data
Jun. 3, 2010 (TR) .............................. a 2010 04461

(51) Int. Cl.
| | |
|---|---|
| *A61K 9/28* | (2006.01) |
| *A61J 3/00* | (2006.01) |
| *A61K 9/48* | (2006.01) |
| *A61J 3/07* | (2006.01) |
| *A61K 9/00* | (2006.01) |
| *A61M 15/00* | (2006.01) |

(52) U.S. Cl.
CPC .............. *A61J 3/005* (2013.01); *A61K 9/4816* (2013.01); *A61M 15/0035* (2014.02); *A61M 15/0038* (2014.02); *A61J 3/07* (2013.01); *A61K 9/0075* (2013.01); *A61M 15/0028* (2013.01); *A61M 2202/062* (2013.01); *A61M 2202/064* (2013.01)

(58) Field of Classification Search
USPC ...................................... 427/2.14; 128/200.23
See application file for complete search history.

(56) References Cited

U.S. PATENT DOCUMENTS

| | | | |
|---|---|---|---|
| 5,641,510 A * | 6/1997 | Clark et al. ................... | 424/451 |
| 6,585,959 B2 * | 7/2003 | Walz et al. ...................... | 424/46 |
| 2005/0121027 A1 | 6/2005 | Nilsson et al. | |

FOREIGN PATENT DOCUMENTS

| | | |
|---|---|---|
| EP | 1508330 A1 | 2/2005 |
| EP | 2172190 A1 | 4/2010 |
| WO | WO-01/78695 A2 | 10/2001 |
| WO | WO-02/30389 A1 | 4/2002 |
| WO | WO-02/30390 A2 | 4/2002 |
| WO | WO-2006/037736 A1 | 4/2006 |
| WO | WO-2007/070851 A2 | 6/2007 |
| WO | WO-2008/084312 A2 | 7/2008 |

OTHER PUBLICATIONS

Search Report for Turkish Application No. TR 2010/04461, mailed Jan. 18, 2012 (19 pages).
Written Opinion and International Search Report for PCT/TR2011/000142 mailed Dec. 14, 2011 (9 pages).

* cited by examiner

*Primary Examiner* — Dah-Wei D Yuan
*Assistant Examiner* — Andrew Bowman
(74) *Attorney, Agent, or Firm* — Clark & Elbing LLP

(57) ABSTRACT

The present invention relates to a process developed for production of a dry powder medicament used in respiratory tract diseases such as asthma and COPD.

17 Claims, No Drawings

PROCESS FOR DRY POWDER FORMULATIONS

CROSS-REFERENCE TO RELATED APPLICATIONS

This application is a national phase application of International Application No. PCT/TR2011/000142, filed on Jun. 2, 2011, which claims benefit of Turkish Application No. 2010/04461, filed on Jun. 3, 2010.

FIELD OF THE INVENTION

The present invention relates to a process used for preparation of a drug in dry powder form developed for the treatment of respiratory tract diseases such as asthma and COPD.

BACKGROUND OF THE INVENTION

Intake of drugs by the inhalation route has an important role to obtain rapid effects in the treatment of respiratory diseases such as asthma and COPD because the drugs delivered by the inhalation route instantly start their activity there when administered directly to the respiratory tract. Compared with the oral and the parenteral route, administration of the drug by the oral route provides the desired effect in a shorter time and at lower doses of the drugs. In addition, possibility of occurrence of side effects is decreased and/or severity of the side effects is alleviated owing to administration of the drug directly to the target area and its use at lower doses. As the active agents taken by the inhalation route in the treatment of respiratory tract diseases are very potent, use of very low doses of these drugs is sufficient in order to obtain the required effect. The active agent is diluted with various excipients in course of production so as to eliminate the problems that would be encountered in production and use as a result of use of the active agent at very low doses. Furthermore, the excipients in the formulation enable to carry the active agents to the respiratory tract of the patient since they adsorb the active agents to their surfaces. Since amount of excipient used in the production of the formulation is quite higher than the amount of active agent, characteristics of the formulation are influenced by the selection and features of the excipient chosen.

Dry powder formulations are generally inhaled from blisters and capsule packs. The most significant factor which negatively affects the pharmaceutical quality of the dry powder formulations developed in order to be inhaled from capsules is moisture. Due to the material they are made of, capsules absorb moisture and the moisture diffuses into the capsule. The medicament exposed to moisture in the capsule is disintegrated in a short time; adheres to the inner surface of the capsule and the medicament is agglomerated. This results in administration of a lower amount of the active agent than the required amount for an effective treatment during the inhalation. Moreover, the capsules exposed to moisture are deformed in time. Therefore, problems occur while the capsules are pierced and/or the capsules cannot be pierced completely. In order to eliminate all these problems; many formulations, new production methods for these formulations and capsules have been developed in the prior art. These methods and capsules developed are generally high priced. In the patent application numbered US20060115432 (A1), a process applied to improve the features of lactose used in the formulation is disclosed. However, no solution is suggested so as to eliminate the problems resulting from the capsule moisture mentioned above. In the patent numbered EP1379220 (B1), a capsule made of a material with reduced moisture content which contains dry powder formulations comprising tiotropium as mixed with a physiologically acceptable excipient is disclosed. However, production of the capsule of materials with reduced moisture content does not bring long term solutions to problems resulting from moisture content of the capsule material. The capsule disclosed in this patent remains incapable in entirely eliminating the possibility of moisture absorption of the capsule due to the humidity of air and the conditions in course of production.

The inventors have developed a process enabling to eliminate or minimize the abovementioned problems for production of formulations comprising active agents effective in the treatment of respiratory tract diseases such as asthma and COPD.

DETAILED DESCRIPTION OF THE INVENTION

The present invention relates to a process developed for production of a dry powder formulation. Said process comprises the following steps:
  the excipient is divided into two fractions,
  each fraction of the excipient is micronized separately and the average particle size of each excipient fraction is ensured to be different from each other,
  the finer excipient fraction is placed into empty capsules,
  the capsules containing the finer excipient fraction is subjected to vibration and particles of the excipient are ensured to cover the inner surfaces of the capsules,
  the coarser excipient fraction and the active agent formulation are mixed,
  the mixture obtained is filled into the capsules, inner surface of which are covered with excipient particles.

The process for preparation of dry powder formulation according to the present invention is characterized in that inner surfaces of the capsules are covered with particles of the finer excipient before the dry powder formulation is filled into the capsules. According to this, direct contact of the inner surface of the capsule and the dry powder formulation filled into the capsule, inner surface of which is covered with excipient particles, is impeded and the moisture diffusing into the capsule is absorbed by the particles covering the inner surface of the capsule. Thus, as mentioned above, problems resulting from the moisture of the capsule material and moisture permeability of the capsule are not experienced.

After the finer excipient fraction is placed in the capsules, the capsules are vibrated by a vibration inducing device for some time, preferably at least for 1 hour, more preferably at least for 2 hours, and thus the excipient particles are ensured to adhere to the inner surfaces of the capsules due to the moisture of the capsule material.

In another aspect, if moisture of the capsule material is insufficient for the excipient particles to entirely cover the inner surface of the capsule, preferably empty capsules are subjected to at least 75% relative humidity at a temperature in the range of 30° C. to 50° C. for at least 1 hour before the finer excipient fraction is placed in the capsules. Conditions of subjection of the capsules to humidity is adjusted such that the inner surface of the capsule is entirely covered with excipient particles. According to this, in the case that the moisture of the capsule material is insufficient for ensuring the excipient particles to cover the inner surface of the capsule completely, empty capsules are more preferably subjected to at least 85% relative humidity preferably at a temperature in the range of 35° C. to 45° C. preferably for at least 2 hours before the finer excipient fraction is placed in the capsules. After the finer excipient fraction is placed in the empty capsules subjected to said operations, the capsules are vibrated by a vibration inducing device for preferably at least 1 hour, more preferably for at least 2 hours and the entire inner surfaces of the capsules are ensured to be covered by excipient particles.

According to another aspect of the process of the present invention, preferably some part of the finer excipient fraction is used to cover the inner surface of the capsules and the rest of it can be added while the coarser excipient fraction and the active agent are mixed, and said finer excipient fraction can be mixed with the coarser excipient fraction and the active agent. In cases where some part of the finer excipient fraction is used to cover the inner surface of the capsules, the amount of said part of finer excipient fraction is at least 25%, preferably in the range of 40-98%, more preferably in the range of 55-95% by weight of the total amount of finer excipient fraction Each fraction of the excipient divided into its fractions in the process of the present invention is micronized such that the average particle size of the finer excipient fraction is in the range of 1 µm to 10 µm, for instance in the range of 1 µm, 2 µm, 3 µm, 4 µm or 5 µm to 6 µm, 7 µm, 8 µm, 9 µm or 10 µm; preferably in the range of 1 µm to 5 µm; more preferably in the range of 1 µm to 3 µm; the average particle size of the coarser excipient fraction is in the range of 20 µm to 1000 µm, for instance in the range of 60 µm, 65 µm, 70 µm, 75 µm, 80 µm, 85 µm, 90 µm, 95 µm, 100 µm or 120 µm to 135 µm, 150 µm, 175 µm, 200 µm, 225 µm, 250 µm, 275 µm, 300 µm, 450 µm, 600 µm, 750 µm, 900 µm or 1000 µm; preferably in the range of 20 µm to 600 µm; more preferably in the range of 20 µm to 300 µm.

The amount of the finer fraction of the excipient fractionated in the process of the present invention by weight is in the range of 1 mg to 50 mg, for instance in the range of 1 mg, 2 mg, 3 mg, 4 mg, 5 mg, 6 mg, 7 mg, 8 mg, 9 mg, 10 mg, 12 mg, 15 mg or 17 mg to 25 mg, 30 mg, 35 mg, 40 mg, 45 mg, 50 mg; preferably in the range of 1 mg to 20 mg; more preferably in the range of 1 mg to 5 mg. The amount of the coarser fraction by weight is in the range of 1 mg to 50 mg, for instance in the range of 1 mg, 2 mg, 3 mg, 4 mg, 5 mg, 6 mg, 7 mg, 8 mg, 9 mg or 10 mg to12 mg, 15 mg, 17 mg, 20 mg, 22 mg, 25 mg, 27 mg, 30 mg, 35 mg, 40 mg, 45 mg, 50 mg; preferably in the range of 3 mg to 25 mg; more preferably in the range of 3 mg to 17 mg. Total weight of the finer excipient fraction is 3%-50%, preferably 5%-45%, more preferably 10%-40% of the total weight of the coarser excipient fraction.

The active agent formulation used in the process according to the present invention is composed of the particles of the active agent and preferably the excipient. In other terms, the active agent formulation can comprise either the particles of both the active agent and the excipient or only the particles of the active agent. In the case that the active agent formulation comprises excipient, particles of the active agent and the excipient are mixed and the active agent formulation is prepared in order to be used in the process of the present invention. The average particle size of the excipient fraction used in the active agent formulation is preferably larger than the average particle size of the excipient fraction used to cover the inner surface of the empty capsule. In other terms, the average particle size of the excipient fraction covering the inner surface of the capsule is preferably smaller than the average particle size of the excipient fraction in the active agent formulation. Thus, excipient particles comprised in the active agent formulation cannot pass through the openings on the covering, and the contact between the active agent formulation and the capsule is minimized since the excipient particles covering the inner surface of the capsule adheres to the inner surface of the capsule more strongly and they are tightly placed on this surface.

The average particle size of the excipient fraction comprised in the active agent formulation is in the range of 2 μm to 45 μm, for instance in the range of 2 μm, 3 μm, 4 μm, 5 μm, 6 μm, 7 μm, 8 μm, 9 μm, 10 μm, 11 μm, 12 μm, 15 μm or 16 μm to 18 μm, 20 μm, 22 μm, 24 μm, 26 μm, 28 μm, 30 μm, 32 μm, 35 μm, 37 μm, 40 μm, 42 μm or 45 μm; more preferably in the range of 2 μm to 35 μm; more preferably in the range of 2 μm to 25 μm. The average particle size of the active agent comprised in the active agent formulation is in the range of 1 μm to 30 μm, for instance in the range of 1 μm, 2 μm, 3 μm, 4 μm or 5 μm to 6 μm, 7 μm, 8 μm, 9 μm, 10 μm, 15 μm, 20 μm, 25 μm or 30 μm; preferably in the range of 1 μm to 10 μm; more preferably in the range of 1 μm to 5 μm.

The amount of the excipient in the active agent formulation used for preparation of the dry powder formulation contained in each capsule is in the range of 0 mg to 12 mg, preferably in the range of 0 mg to 10 mg, more preferably in the range of 0 mg to 5 mg. The amount of active agent in the active agent formulation used for preparation of the dry powder formulation contained in each capsule is in the range of 0.001 mg to 12 mg, preferably in the range of 0.001 mg to 8 mg, more preferably in the range of 0.001 mg to 5 mg.

In the process of the present invention, a dry powder formulation is prepared by mixing the coarser excipient fraction and the active agent formulation in order to fill the capsules, inner surfaces of which are covered with the particles of the finer excipient fraction. In the case that preferably some part of the finer excipient fraction is placed in the capsules so as to cover the inner surface of the capsules, in course of preparation of said dry powder formulation preferably primarily rest of the finer excipient fraction and the active agent formulation are mixed, and then this mixture is mixed with the coarser excipient fraction and a dry powder formulation is obtained this way. The obtained dry powder formulation is filled into the capsules, inner surface of which are covered with excipient particles.

The process of the present invention provides to eliminate or minimize the problems resulting from the moisture and moisture permeability of the capsule encountered in dry powder formulations inhaled from capsules. According to this, the problems such as adhesion of the particles to inner surfaces of capsules, agglomeration of the particles in the formulation, deterioration of the active agent, deformation of the capsules resulting from capsule moisture are eliminated or minimized in the dry powder formulation produced using the process of the present invention. Therefore, required amount of the active agent is ensured to be delivered to the patient in the dry powder formulations prepared by using the process of the present invention. Furthermore, the active agent comprised in the formulation is provided to be inhaled by good dosage preciseness and the formulation is ensured to be inhaled with a proper particle size distribution in each inhalation since the agglomeration of the particles of the dry powder formulation contained in the capsule and their adhesion to the inner surfaces of the capsules are prevented.

In another aspect, covering the inner surfaces of the capsules with the finer excipient fraction according to the process of the present invention impedes deformations of the capsules resulting from the moisture of the capsule material. This is because of the fact that covering the inner surfaces of the capsules with the finer excipient fraction enables the capsule material both to maintain optimum firmness and remain stable for long periods of time.

In another aspect, the present invention provides a dry powder formulation comprising at least two excipient fractions having different average particle sizes in addition to the active agent. Since the amount of the active agents used in the treatment of respiratory diseases is quite low, the active agents are diluted with excipients in order to eliminate the problems that would be encountered during production and inhalation. Furthermore, the excipient particles in the formulation also ensure to carry the particles of the active agent to the respiratory tract of the patient during inhalation as well as diluting the active agent particles.

As the amount of the excipient in the formulation prepared is quite higher than the amount of active agent, characteristics of the formulation are influenced by the selection and features of the excipient chosen to a substantial extent. To this respect, the amount of the active agent comprised in the formulation delivered to the respiratory tract of the patient is considerably influenced by the particle size and the amount of the excipient used in the formulation. The fact that the dry powder formulation according to the process of the present invention comprises at least two excipient fractions with different average particle sizes at the specified amounts provides the active agent of the formulation to be homogeneously distributed in the formulation and therefore the active agent to be present in each capsule with a good measurement preciseness and an effective amount of the active agent in the formulation to be delivered to the respiratory tract of the patient during inhalation.

In another aspect, the dry powder formulation produced using the process of the present invention is administered via a dry powder inhaler enabling the inhalation of the dry powder formulation from capsules. In the inhalers enabling the inhalation of the dry powder formulation from capsules, the capsule is pierced or cut and the dry powder formulation in the capsule becomes ready for inhalation in response to each actuation of the device.

The capsule used in the inhaler described above can be made of any suitable substance though it is preferably made of a substance selected from the group comprising gelatin, chitosan, starch and/or starch derivatives, cellulose and/or cellulose derivatives or synthetic polymers and it is composed of intertwining top and bottom compartments. The top and the bottom compartments of the capsule can be made of identical or different materials.

According to this, in the case that the capsule used in the present invention is made of cellulose or its derivatives, the capsule material can be selected from, but not limited to, a group comprising hydroxypropyl cellulose, hydroxypropylmethyl cellulose, methyl cellulose, hydroxymethyl cellulose, hydroxyethyl cellulose.

In the case that the capsule used in the present invention is synthetic polymer, the capsule material can be selected from, but not limited to, a group comprising polyethylene, polyetheleneteraphtalate, polycarbonate or polypropylene.

In the case that the capsule material used in the present invention is gelatine, additional agents such as polyethylene glycol, sorbitol, glycerol, propylene glycol, polyethylene oxide-polypropylene oxide block copolymers and/or other polyalcohols and polyethers at different molecular weights can be added into it.

The excipient comprised in the dry powder formulation prepared using the process of the present invention is selected from a group comprising monosaccharides (glucose, etc.), disaccharides (lactose, cellobiose, saccharose, maltose, etc.), oligosaccharides and polysaccharides (dextran, etc.), polyalcohols (sorbitol, mannitol, xylitol, etc.), salts (sodium chloride, calcium carbonate, etc.), inositol and/or isomers thereof (myoinositol, etc.) or a combination thereof. The excipient comprised in said dry powder formulation is lactose, preferably alpha-lactose.

The active agent formulation in the process of the present invention comprises at least one active agent selected from the group comprising anticholinergic, adrenergic agonist, glucocorticosteroid, xanthine, anti-leukotriene, PDE IV inhibitor, EGFR inhibitor, anti-allergic, anti-inflammatory, antihistaminic and anti-muscarinic agents and a combination thereof.

The active agent formulation used in the process of the present invention comprises one or more active agents selected from the group consisting of anticholinergics such as tiotropium, ipratropium, glicopirronium, oxytropium; $\beta_2$-agonists such as formoterol, arformoterol, bambuterol, salmeterol, carmoterol, clenbuterol, salbutamol, fenoterol, terbutaline, carbuterol, pirbuterol; corticosteroids such as beclomethasone, budesonide, ciclesonide, fluticasone and mometasone; xanthines such as doxophylline, theobromine, theophylline and aminophylline; anti-leukotrienes such as montelukast, pranlukast, zafirlukast, ritolukast, sulukast, tomelukast, verlukast, iralukast, ablukast ye cinalukast; antihistamines such as cetirizine, levocetirizine, loratadine, desloratadine, clemastine, chlorphenamine, diphenhydramine and pheniramine; PDE IV inhibitors such as roflumilast, piclamilast and cilomilast; and antihistamines such as levocetirizine, desloratadine, cetirizine, loratadine, fexofenadine, setastine and terfenadine. The active agent formulation used in the process of the present invention preferably comprises at least one active agent selected from a group comprising tiotropium, carmoterol, formoterol, arformoterol, salmeterol, budesonide, ciclesonide, fluticasone, mometasone and combinations thereof.

The dry powder medicament prepared according to the process of the present invention is used in the treatment of many respiratory diseases, particularly in allergic or non-allergic asthma, allergic rhinitis and chronic obstructive pulmonary disease (COPD). Accordingly, the dry powder formulation prepared according to the process of the present invention is used in the treatment of, but not limited to, asthma at any stages, acute lung injury (ALI), acute respiratory distress syndrome (ARDS), exacerbation of airway hyperactivity, bronchiectasis, chronic obstructive pulmonary including emphysema and chronic bronchitis, respiratory diseases or lung diseases (COPD, COAD or COLD), pneumoconiosis, aluminosis, anthracosis, asbestosis, chalicosis, ptilosis, siderosis, silicosis, tabacosis, byssinosis.

The examples below are given in order to provide better understanding of the present invention, yet they do not limit the scope of the invention.

EXAMPLE 1

In preparation of a dry powder formulation suitable for administration via a dry powder inhaler developed for inhalation of the dry powder formulation from capsules, 13.8 mg lactose is divided into two fractions. One of these fractions is 2.1 mg while the other one is 11.7 mg. The excipient fraction weighting 2.1 mg is micronized such that its average particle size is 5.3 μm; the excipient fraction weighting 11.7 mg is micronized such that its average particle size is 168 μm. The excipient fraction with the average particle size of 5.3 μm is placed in empty capsules, and the inner surfaces of the capsules are ensured to be covered with the excipient particles by vibrating the capsules by a vibration inducing device for 2.75 hours. On the other hand, 12 μg formoterol with an average particle size of 4 μm; 400 μg budesonide with an average particle size of 4 μm and 4.1 mg excipient with an average particle size of 8 μm are mixed and the active agent formulation is prepared. The active agent formulation prepared is mixed with the excipient fraction with an average particle size of 168 μm and the dry powder formulation is obtained so as to be placed in the capsules. The dry powder formulation prepared is placed in the capsules, inner surfaces of which are covered with excipient particles and the capsules prepared are placed in blister packs. Results of the analyses of 10 capsules comprising this formulation conducted by NGI device in order to determine FPF (fine particle fraction %) values of the dry powder formulation prepared as described above are given in the table below.

| | Example | | | | | | | | | |
|---|---|---|---|---|---|---|---|---|---|---|
| | 1 | 2 | 3 | 4 | 5 | 6 | 7 | 8 | 9 | 10 |
| FPF % | 29.5 | 32.5 | 31.2 | 28.9 | 31.5 | 32.2 | 29.9 | 29.6 | 30.3 | 31.5 |

EXAMPLE 2

In preparation of a dry powder formulation suitable for administration via a dry powder inhaler developed for inhalation of the dry powder formulation from capsules, 17.5 mg lactose is divided into two fractions. One of these fractions is 4.2 mg while the other one is 13.3 mg. The excipient fraction weighting 4.2 mg is micronized such that its average particle size is 3.9 μm; the excipient fraction weighting 13.3 mg is micronized such that its average particle size is 187 μm. 2.8 mg of the excipient fraction with the average particle size of 3.9 μm is placed in empty capsules, and the inner surfaces of the capsules are ensured to be covered with excipient particles by vibrating the capsules by a vibration inducing device for 3.25 hours. On the other hand, 100 μg ciclesonide with an average particle size of 3.5 μm; 18 μg tiotropium with an average particle size of 3.6 μm and 3.8 mg excipient with an average particle size of 7.5 μm are mixed and the active agent formulation is prepared. The active agent formulation prepared is mixed with the excipient fraction with an average particle size of 187 μm and the rest of the excipient fraction with an average particle size of 3.9 μm, and dry powder formulation is obtained so as to be placed in capsules. The dry powder formulation prepared is placed in the capsules, inner surfaces of which are covered with excipient particles and the capsules prepared are placed in blister packs. Results of the analyses of 10 capsules comprising this formulation conducted by NGI device in order to determine FPF (fine particle fraction %) values of the dry powder formulation prepared as described above are given in the table below.

| | Example | | | | | | | | | |
|---|---|---|---|---|---|---|---|---|---|---|
| | 1 | 2 | 3 | 4 | 5 | 6 | 7 | 8 | 9 | 10 |
| FPF % | 30.5 | 31.9 | 32.6 | 32.3 | 32.8 | 31.0 | 30.2 | 31.4 | 29.8 | 30.8 |

EXAMPLE 3

In preparation of a dry powder formulation suitable for administration via a dry powder inhaler developed for inhalation of the dry powder formulation from capsules, 9.2 mg lactose is divided into two fractions. One of these fractions is 1.4 mg while the other one is 7.8 mg. The excipient fraction weighting 1.4 mg is micronized such that its average particle size is 3.6 μm; the excipient fraction that is 7.8 mg is micronized such that its average particle size is 202 μm. Before the excipient fraction with the average particle size of 3.6 μm is placed in empty capsules, the empty capsules are subjected to 85% relative humidity at a temperature of 45° C. for 1.5 hours. Then, the excipient fraction with the average particle size of 3.6 μm is placed in the empty capsules and the inner surfaces of the capsules are ensured to be covered with excipient particles by vibrating the capsules by a vibration inducing device for 2.25 hours. On the other hand, 250 μg fluticasone with an average particle size of 3.8 μm; 50 μg salmeterol with an average particle size of 4.0 μm and 1.2 mg excipient with an average particle size of 8.2 μm are mixed and the active agent formulation is prepared. The active agent formulation prepared is mixed with the excipient fraction with an average particle size of 202 μm and the dry powder formulation is obtained so as to place in capsules. The dry powder formulation prepared is placed in the capsules, inner surfaces of which are covered with excipient particles and the capsules prepared are placed in blister packs. Results of the analyses of 10 capsules comprising this formulation conducted by NGI device in order to determine FPF (fine particle fraction %) values of the dry powder formulation prepared as described above are given in the table below.

| Example | 1 | 2 | 3 | 4 | 5 | 6 | 7 | 8 | 9 | 10 |
|---|---|---|---|---|---|---|---|---|---|---|
| FPF % | 31.1 | 32.5 | 32.5 | 33.2 | 32.9 | 31.8 | 30.6 | 31.7 | 33.6 | 32.5 |

The invention claimed is:

1. A process for producing a dry powder formulation, comprising the steps of:

a) dividing an excipient into two fractions, wherein each fraction of the excipient is micronized separately and the average particle size of each excipient fraction is different;

b) placing the finer excipient fraction into empty capsules, wherein the capsules containing the finer excipient fraction is subjected to vibration ensuring that the particles of the finer excipient fraction cover the inner surfaces of the capsules;

c) mixing the coarser excipient fraction and an active agent formulation to obtain a mixture; and d) filing the mixture into the capsules, wherein the inner surfaces of the capsules are covered with the finer excipient particles, wherein the empty capsules are subjected to at least 75% relative humidity at a temperature in the range of 30° C. to 50° C. for at least 1 hour before the finer excipient fraction is placed in the capsules.

2. The process according to claim 1, wherein the empty capsules are subjected to at least 85% relative humidity at a temperature in the range of 35° C. to 45° C. for at least 2 hours before the finer excipient fraction is placed in the capsules.

3. A process for producing a dry powder formulation, comprising the steps of:
   a) dividing an excipient into two fractions, wherein each fraction of the excipient is micronized separately and the average particle size of each excipient fraction is different;
   b) placing the finer excipient fraction into empty capsules, wherein the capsules containing the finer excipient fraction is subjected to vibration ensuring that the particles of the finer excipient fraction cover the inner surfaces of the capsules;
   c) mixing the coarser excipient fraction and an active agent formulation to obtain a mixture; and
   d) filing the mixture into the capsules, wherein the inner surfaces of the capsules are covered with the finer excipient particles, wherein some part of the finer excipient fraction is used to cover the inner surface of the capsules while the rest is mixed with the coarser excipient fraction and the active agent formulation.

4. A process for producing a dry powder formulation, comprising the steps of:
   a) dividing an excipient into two fractions, wherein each fraction of the excipient is micronized separately and the average particle size of each excipient fraction is different;
   b) placing the finer excipient fraction into empty capsules, wherein the capsules containing the finer excipient fraction is subjected to vibration ensuring that the particles of the finer excipient fraction cover the inner surfaces of the capsules;
   c) mixing the coarser excipient fraction and an active agent formulation to obtain a mixture; and
   d) filing the mixture into the capsules, wherein the inner surfaces of the capsules are covered with the finer excipient particles, wherein the total weight of the finer excipient fraction is in the range of 3% to 50% of the total weight of the coarser excipient fraction.

5. The process according to claim 4, wherein said excipient is selected from a group comprising monosaccharides (glucose, etc.), disaccharides (lactose, cellobiose, saccharose, maltose, etc.), oligosaccharides and polysaccharides (dextran, etc.), polyalcohols (sorbitol, mannitol, xylitol, etc.), salts (sodium chloride, calcium carbonate, etc.), inositol and/or isomers thereof (myoinositol, etc.) or a combination thereof.

6. The process according to claim 5, wherein said excipient is lactose.

7. The process according to claim 4, wherein said active agent formulation comprises at least one active agent selected from the group consisting of anticholinergic, adrenergic agonist, glucocorticosteroid, xanthine, anti-leukotriene, PDE IV inhibitor, EGFR inhibitor, anti-allergic, anti-inflammatory, antihistaminic and anti-muscarinic agents, and a combination thereof.

8. The process according to claim 7, wherein said active agent formulation comprises one or more active agents selected from the group consisting of anticholinergics; β2-agonists; antihistamines; and PDE IV.

9. The process according to claim 8, wherein said active agent formulation comprises at least one active agent selected from a group consisting of tiotropium, carmoterol, formoterol, arformoterol, salmeterol, budesonide, ciclesonide, fluticasone, mometasone, and combinations thereof.

10. The process according to claim 8, wherein said anticholinergic is tiotropium, ipratropium, glicopirronium, or oxytropium; wherein said β2-agonist is formoterol, arformoterol, bambuterol, salmeterol, carmoterol, clenbuterol, salbutamol, fenoterol, terbutaline, carbuterol, or pirbuterol; wherein said corticosteroid is beclomethasone, budesonide, ciclesonide, fluticasone and mometasone; xanthines such as doxophylline, theobromine, theophylline, or aminophylline; wherein said xanthine is doxophylline, theobromine, theophylline and aminophylline; anti-leukotrienes such as montelukast, pranlukast, zafirlukast, ritolukast, sulukast, tomelukast, verlukast, iralukast, ablukast ve cinalukast; wherein said antihistamine is cetirizine, levocetirizine, loratadine, desloratadine, clemastine, chlorphenamine, diphenhydramine, pheniramine, fexofenadine, setastine, or terfenadine.; or wherein said PDE IV inhibitor is roflumilast, piclamilast, or cilomilast.

11. The process according to claim 4, wherein the empty capsules are subjected to at least 75% relative humidity at a temperature in the range of 30° C. to 50° C. for at least 1 hour before the finer excipient fraction is placed in the capsules.

12. The process according to claim 4, wherein the empty capsules are subjected to at least 85% relative humidity at a temperature in the range of 35° C. to 45° C. for at least 2 hours before the finer excipient fraction is placed in the capsules.

13. The process according to claim 4, wherein the capsules containing the finer excipient fraction are vibrated by a vibration inducing device for at least 1 hour.

14. The process according to claim 4, wherein the capsules containing the finer excipient fraction are vibrated by a vibration inducing device for at least 2 hours.

15. The process according to claim 4, wherein some part of the finer excipient fraction is used to cover the inner surface of the capsules while the rest is mixed with the coarser excipient fraction and the active agent formulation mixture.

16. The process according to claim 4, wherein the average particle size of the combined coarser and finer excipient fractions in the mixture with the active agent formulation is larger than the average particle size of the finer excipient fraction used to cover the inner surfaces of the capsules.

17. The process according to claim 4, wherein the amount of the coarser excipient fraction is in the range of 1 mg to 50 mg.

* * * * *